United States Patent [19]
Grilliot et al.

[11] Patent Number: 5,926,854
[45] Date of Patent: Jul. 27, 1999

[54] PROTECTIVE HELMET AND EYE PROTECTOR ASSEMBLY HAVING FABRIC PANEL FORMING FABRIC COVER FOR EYE PROTECTOR

[75] Inventors: William L. Grilliot; Mary I. Grilliot, both of Dayton, Ohio

[73] Assignee: Norcross Safety Products, L.L.C., Oak Brook, Ill.

[21] Appl. No.: 09/033,640

[22] Filed: Mar. 3, 1998

[51] Int. Cl.⁶ .................................................. A42B 3/18
[52] U.S. Cl. .................................................. 2/424; 2/422
[58] Field of Search .................................. 2/6.2, 6.3, 6.5, 2/6.7, 9, 209.13, 422, 424, 10, 13

[56] References Cited

U.S. PATENT DOCUMENTS

| | | |
|---|---|---|
| 1,033,518 | 7/1912 | Bader . |
| 1,133,056 | 3/1915 | Pachner . |
| 1,170,462 | 2/1916 | Schroeder . |
| 1,696,198 | 12/1928 | Gross . |
| 2,172,296 | 9/1939 | Simkos . |
| 2,277,090 | 3/1942 | Feiler ............................................. 2/8 |
| 2,302,231 | 11/1942 | Lobelle .......................................... 2/10 |
| 2,601,149 | 6/1952 | Jamison, Jr. .................................... 2/5 |
| 2,817,087 | 12/1957 | Rush ............................................. 2/8 |
| 3,066,305 | 12/1962 | Aileo ............................................. 2/6 |
| 3,808,604 | 5/1974 | Rose .............................................. 2/10 |
| 4,179,753 | 12/1979 | Aronberg et al. ........................... 2/422 |
| 4,766,609 | 8/1988 | Lane .............................................. 2/5 |
| 5,012,528 | 5/1991 | Pernicka et al. ............................. 2/10 |
| 5,018,220 | 5/1991 | Lane et al. ..................................... 2/5 |
| 5,105,475 | 4/1992 | Lynd et al. ................................... 2/10 |
| 5,555,569 | 9/1996 | Lane ............................................. 2/424 |

*Primary Examiner*—Diana L. Oleksa
*Attorney, Agent, or Firm*—Rockey, Milnamow & Katz, Ltd.

[57] ABSTRACT

In an assembly comprising a protective helmet and an eye protector, which is adjustable between a usage position and a storage position, a fabric panel has a portion affixed to the protective helmet and a portion extending from the affixed position. The extending portion is adapted to wrap a portion of the eye protector and to be releasably fastenable to the affixed portion so as to form a fabric cover from the fabric panel. The fabric cover is adapted to secure the eye protector in the storage position and to protect the wrapped portion of the eye protector in the storage position against soiling. A hook-and-pile fastener is used to fasten the extending portion of the fabric panel to the affixed portion of the fabric panel. In one contemplated embodiment, the eye protector is a face shield. In another such embodiment, the eye protector is a pair of goggles.

14 Claims, 5 Drawing Sheets

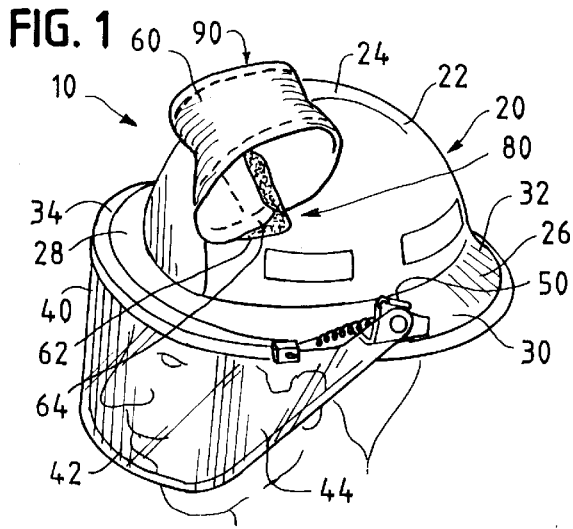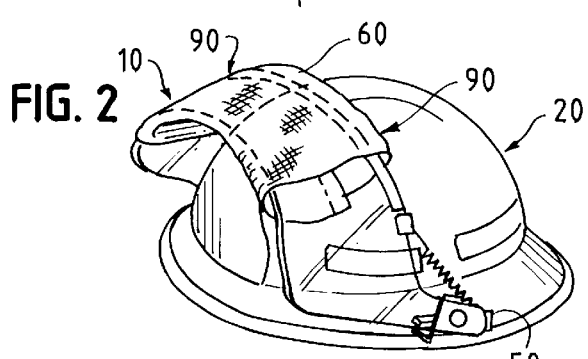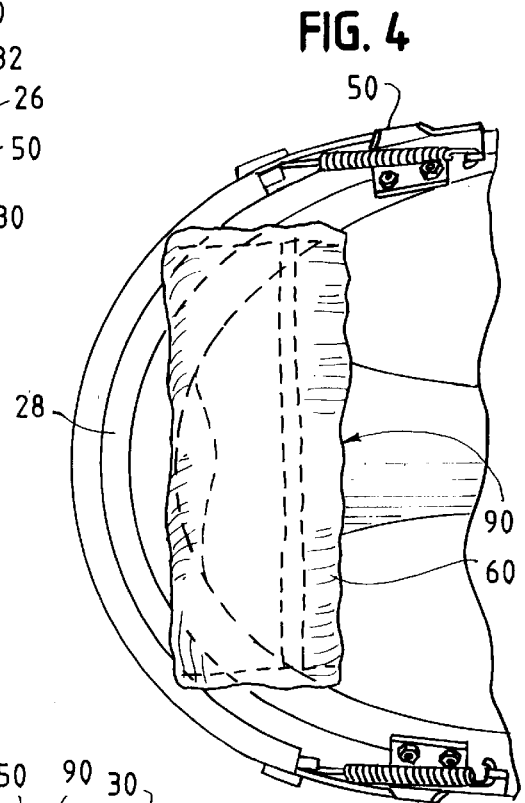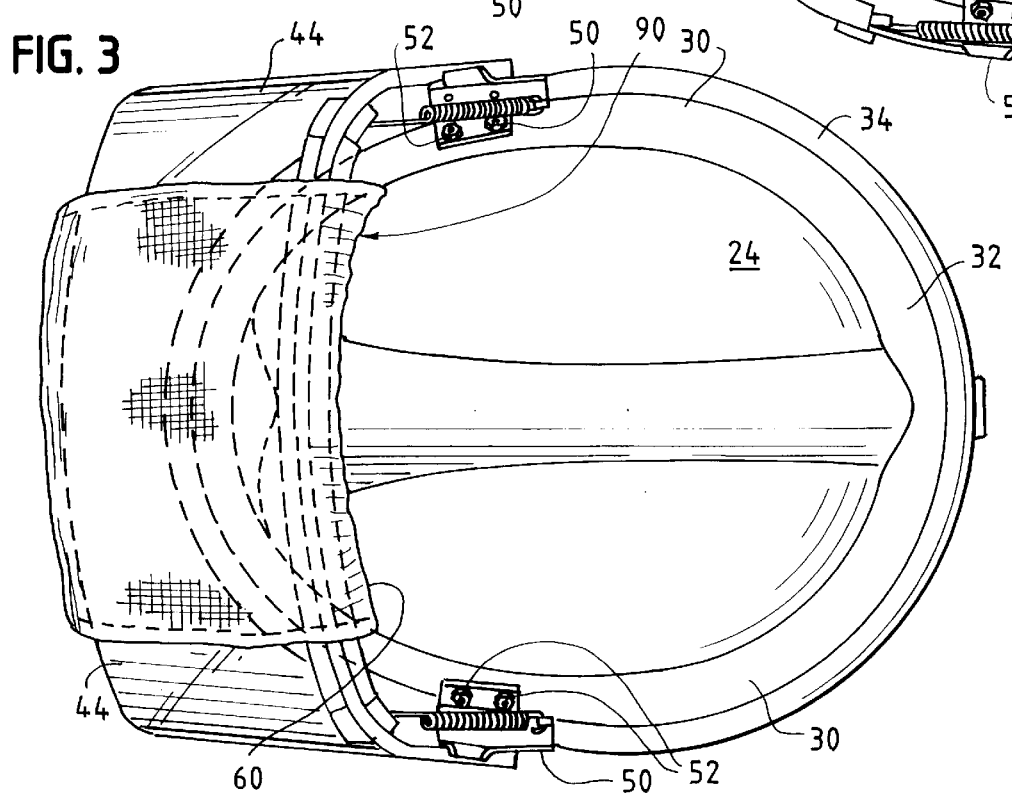

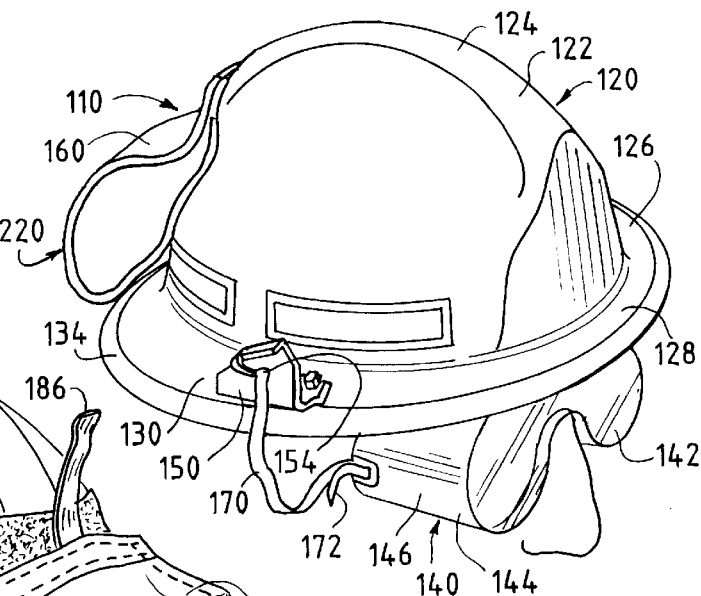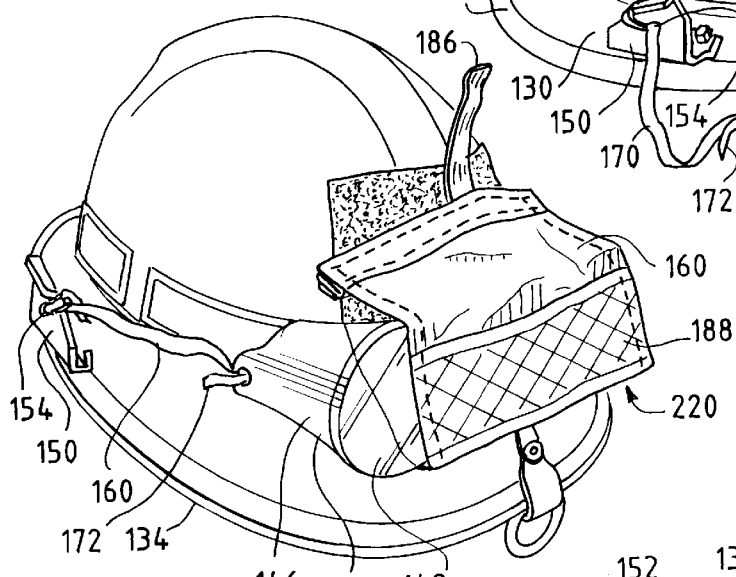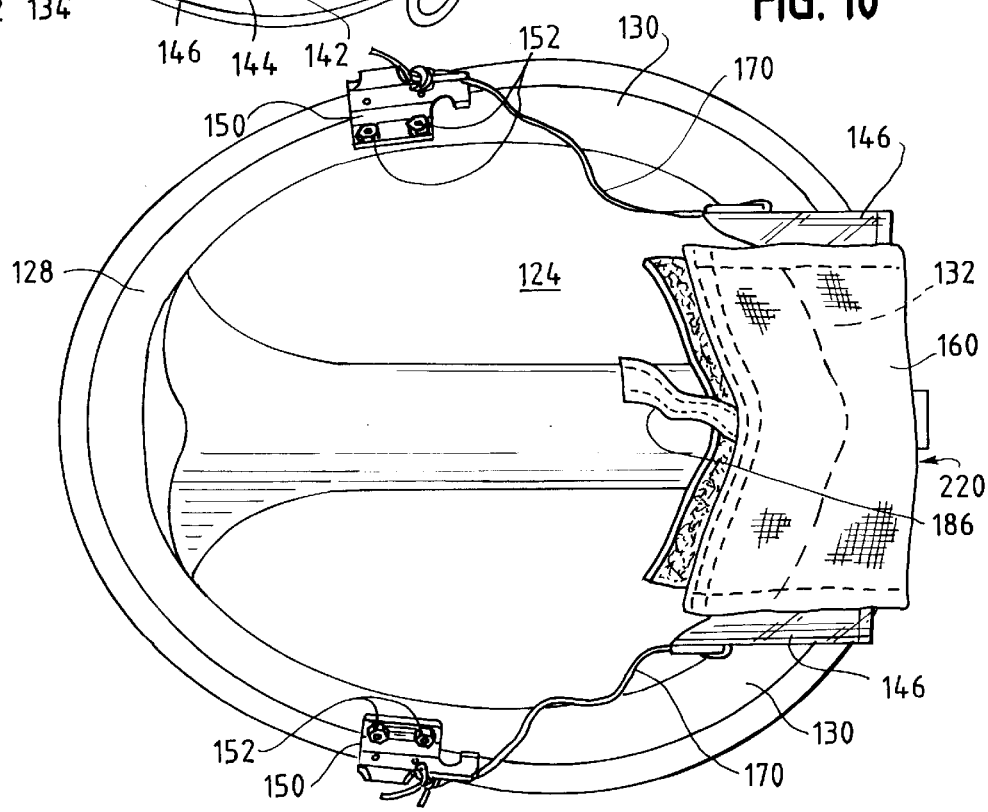

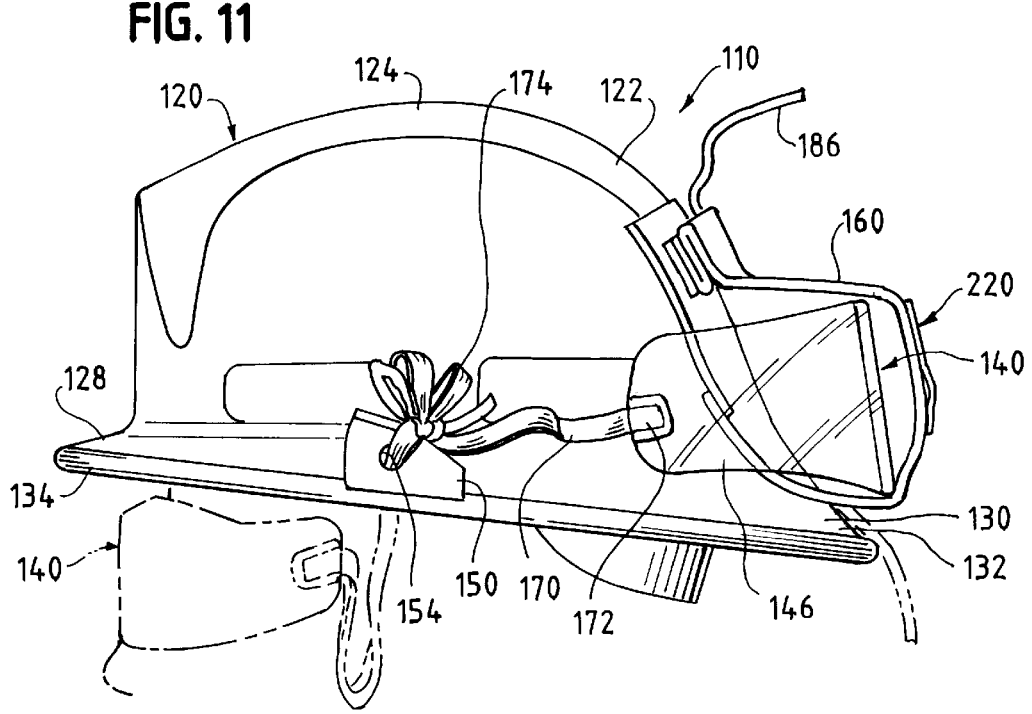
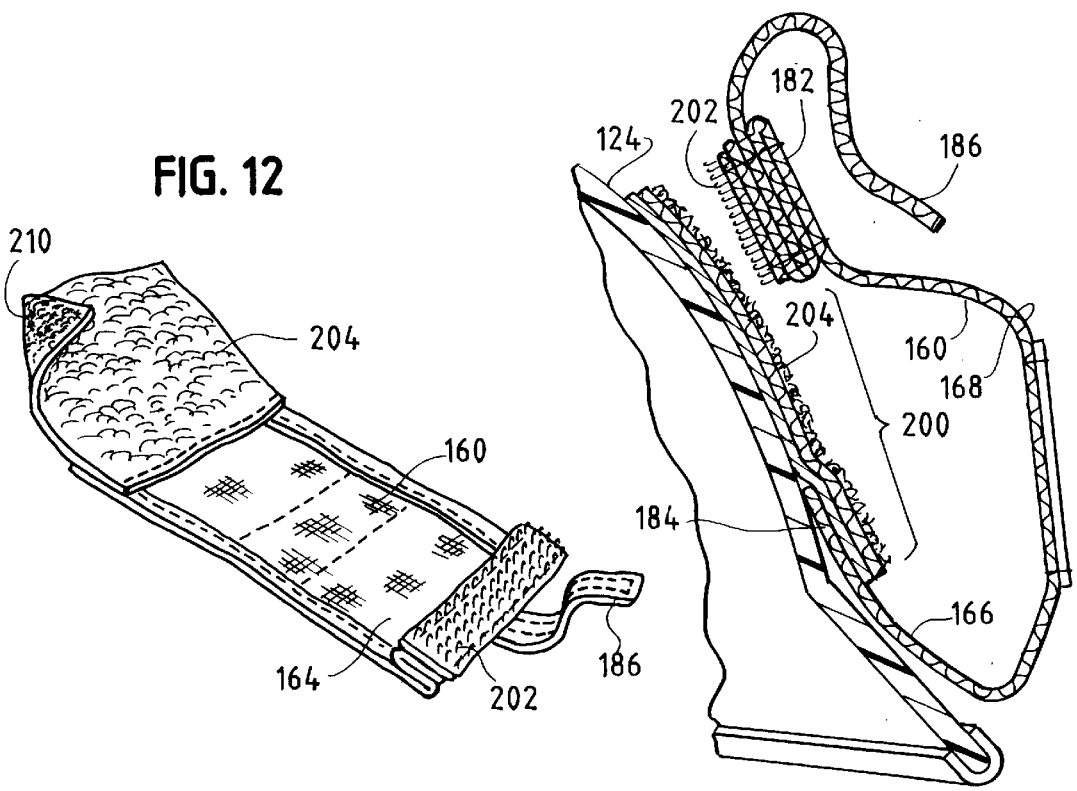

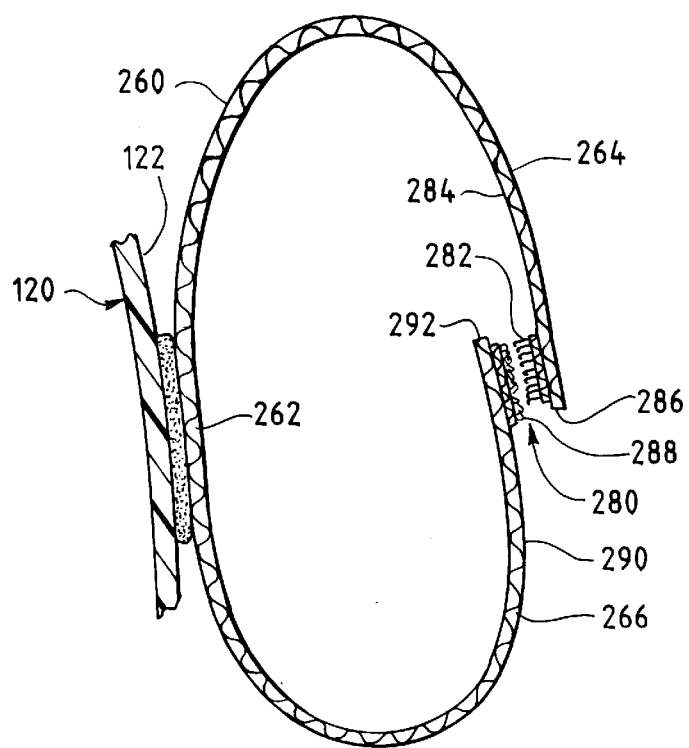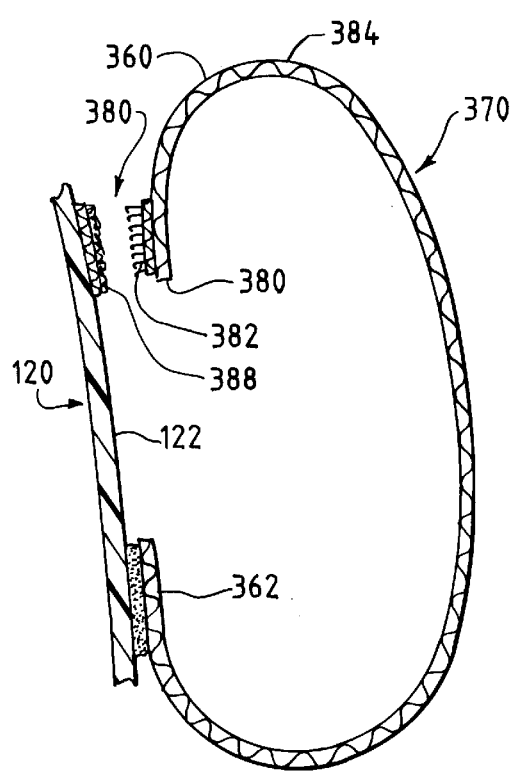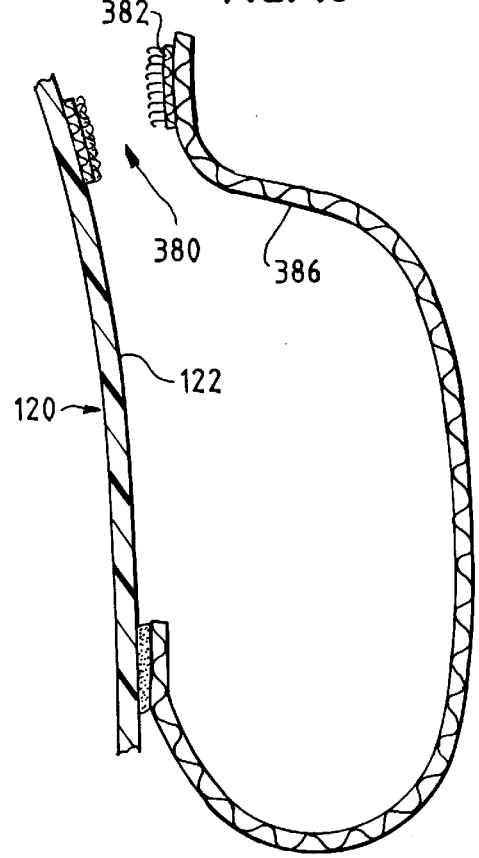

5,926,854

PROTECTIVE HELMET AND EYE PROTECTOR ASSEMBLY HAVING FABRIC PANEL FORMING FABRIC COVER FOR EYE PROTECTOR

TECHNICAL FIELD OF THE INVENTION

This invention pertains to an assembly comprising a protective helmet, such as a firefighter's helmet, and an eye protector that is adjustable between a usage position and a storage position. This invention provides the assembly with a fabric panel, which forms a fabric cover that is adapted to secure the eye protector in the storage position and to protect a wrapped portion of the eye protector in the storage position against soiling, as by soot.

BACKGROUND OF THE INVENTION

As exemplified in Lane U.S. Pat. No. 4,766,609, and U.S. Pat. No. 5,555,569, a protective helmet, such as a firefighter's helmet, has a hard shell having a dome portion and having a rim portion, which projects outwardly from the dome portion and which from a wearer's viewpoint has a front region, two side regions, and a back region.

Commonly, the protective helmet is equipped with an eye protector, either a face shield that protects not only a wearer's eyes but also other portions of the wearer's face or a pair of goggles that protect a wearer's eyes. Commonly, if the eye protector is a face shield, the face shield is hinged to the hard shell of the protective helmet via a pair of hinges mounted to such shell, one hinge on each side, in a manner exemplified in Lane U.S. Pat. No. 4,766,609. Commonly, if the eye protector is a pair of goggles, a pair of ribbons are used to tie the pair of goggles to the hard shell of the protective helmet.

Numerous examples of firefighters' helmets equipped with face shields or with goggles are offered in the 1998 Catalog of Morning Pride Manufacturing, Inc. of Dayton, Ohio. Similar helmets equipped similarly are worn by rescue workers and others.

In a firefighting environment, a face shield or a pair of goggles tends to become soiled with soot from unburned carbon particles, which tend to be very difficult to clean from a face shield or from a pair of goggles. When it is necessary for a firefighter to wear a face shield or a pair of goggles, soiling from soot may be then unavoidable.

A need has arisen, to this invention is addressed, to protect a face shield or a pair of goggles against soiling from soot when it is unnecessary for a firefighter to wear the face shield or the pair of goggles.

SUMMARY OF THE INVENTION

This invention provides a novel assembly comprising a protective helmet, such as a firefighter's helmet, and an eye protector, such as a face shield or a pair of goggles, which is adjustable between a usage position and a storage position. This invention provides the assembly with a fabric panel, which forms a fabric cover that is adapted to secure the eye protector in the storage position and to protect a wrapped portion of the eye protector in the storage position against soiling, as by soot.

The protective helmet is similar to protective helmets known heretofore in that the protective helmet has a hard shell, in that the hard shell has a dome portion and a rim portion, and in that the rim portion has a front region, two side regions, and a back region. Otherwise, this invention is not limited to a protective helmet of any particular form.

The eye protector is similar to eye protectors known heretofore in that the eye protector has two side portions, each of which is attached to the helmet so as to enable a wearer to adjust the eye protector between a usage position beneath the front region of the rim portion and a storage position. Although two embodiments of this invention are contemplated, namely an embodiment wherein the eye protector is a face shield and an embodiment wherein the eye protector is a pair of goggles, this invention is not limited to an eye protector of any particular form or to the contemplated embodiments.

As provided by this invention, the fabric panel has a portion affixed to the hard shell and a portion extending from the affixed portion. The extending portion is adapted to wrap a portion of the eye protector in the storage position and to be releasably fastenable so as to form a fabric cover from the fabric panel. Thus, the fabric cover is adapted to secure the eye protector in the storage position and to protect the wrapped portion of the eye protector in the storage position against soiling, as by soot. Desirably, a heat-resistant, flame-resistant fabric is employed for the fabric panel.

In the contemplated embodiment wherein the eye protector is a face shield, the protective helmet has two hinges, each of which is mounted to a respective one of the side regions of the hard shell. The face shield is hinged to the protective helmet, via the hinges, so as to enable a wearer to adjust the face shield between the usage position and the storage position, which preferably is above the front region of the hard shell. The face shield may be thus hinged to the protective helmet in a manner disclosed in Lane U.S. Pat. No. 4,766,609, the disclosure of which is incorporated herein by reference.

In the contemplated embodiment wherein the eye protector is a pair of goggles having a pair of ribbons, the protective helmet has two brackets, each of which is mounted to a respective one of the side regions of the hard shell. Each ribbon extends between a respective one of the side portions of the pair of goggles and a corresponding one of the brackets, so as to enable a wearer to adjust the face shield between the usage position and the storage position, which preferably is above the back region of the hard shell.

Preferably, in either contemplated embodiment, a fastener is provided, which is adapted to fasten the extending portion of the fabric panel releasably to the affixed portion of the fabric panel so as to form the fabric cover from the fabric panel. Preferably, the fastener is a hook-and-loop fastener, which includes a hook-faced panel and a loop-faced panel with one said fastener panel being sewn to the extending portion of the fabric panel and with the other fastener panel having a portion sewn to the fabric panel and a portion affixed adhesively to the dome portion of the hard shell.

Preferably, in the contemplated embodiment wherein the eye protector is a face shield, the hook-faced and loop-faced panels are sewn to opposite surfaces of the fabric panel. Preferably, in the contemplated embodiment wherein the eye protector is a pair of goggles, the hook-faced and loop-faced panels are sewn to the same side of the fabric panel.

Herein, the term "fabric" is to be broadly understood to cover various cloth and cloth-like materials, whether knitted, woven, non-woven, foamed, laminated, or made similarly or dissimilarly.

These and other objects, features, and advantages of this invention are evident from the following description of two contemplated embodiments of this invention, with reference to the accompanying drawings.

BRIEF DESCRIPTION OF THE DRAWINGS

FIG. 1 is a perspective view of a novel assembly comprising a protective helmet having a hard shell, an eye protector being a face shield, and a fabric panel, which is shown as forming a fabric cover. The face shield is shown in a usage position. A wearer is shown fragmentarily.

FIG. 2 is a similar view showing the face shield in a storage position, in which the face shield is wrapped by the fabric panel and is stored in the fabric cover. The wearer is not shown.

FIG. 3, on a larger scale, is a plan view of the novel assembly, as shown in FIG. 1.

FIG. 4, on a similar scale, is a plan view of the novel assembly, as shown in FIG. 2.

FIG. 8 is a perspective view of a novel assembly comprising a protective helmet having a hard shell, an eye protector being a pair of goggles, and a fabric panel, which is shown as forming a fabric cover. The pair of goggles is shown in a usage position. A wearer is shown fragmentarily.

FIG. 9 is a similar view showing the pair of goggles in a storage position, in which the face shield is wrapped by the fabric panel and is stored in the fabric cover. The wearer is not shown.

FIG. 10, on a larger scale, is a plan view of the novel assembly, as shown in FIG. 9.

FIG. 11, on a similar scale, is a plan view of the novel assembly, as shown in FIG. 10.

FIG. 12, on a similar scale, is a side view of the novel assembly, as shown in FIG. 10.

FIG. 13, on a similar scale, is a perspective view of the fabric panel, apart from the protective helmet, from the novel assembly of FIG. 8.

FIGS. 14, 15, and 16, on a further enlarged scale, are fragmentary, sectional details of three alternative embodiments.

DETAILED DESCRIPTION OF THE ILLUSTRATED EMBODIMENTS

Figure 5:
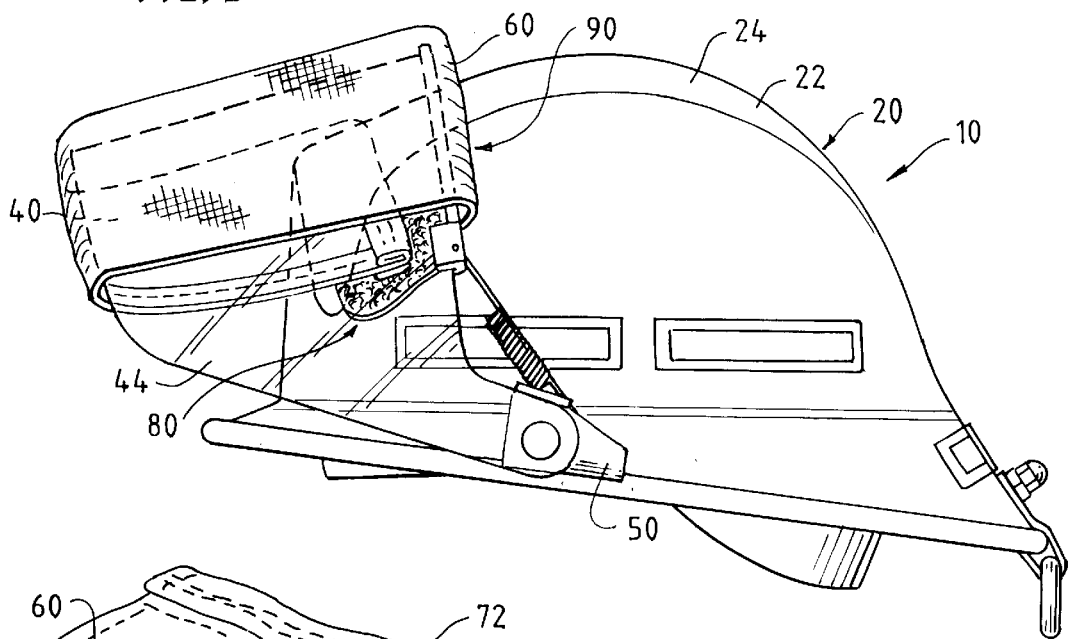
FIG. 5, on a similar scale, is a side view of the novel assembly, as shown in FIG. 2.
Figure 6:
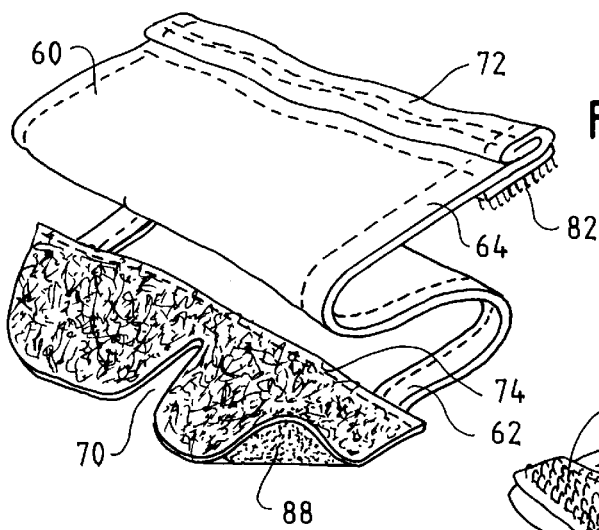
FIG. 6, on a similar scale, is a perspective view of the fabric panel, apart from the protective helmet, from the novel assembly of FIG. 1.
Figure 7:
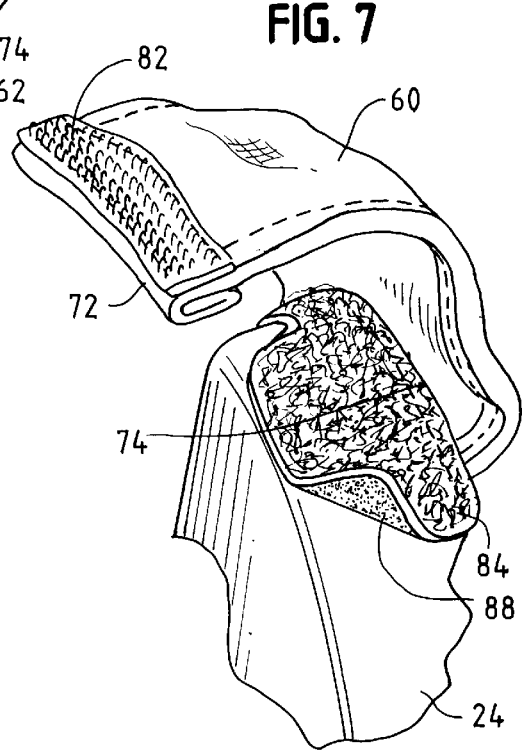
FIG. 7, on a similar scale, is a fragmentary, perspective view of the fabric panel and a fragmentary portion of the hard shell, where a portion of the fabric panel is affixed to the hard shell in the novel assembly of FIG. 1.

As illustrated in FIGS. 1 through 7, a novel assembly 10 constituting one contemplated embodiment of this invention comprises a protective helmet 20, a face shield 40, and a fabric panel 60. As explained below, although the protective helmet 20 and the face shield 40 are known elements, the fabric panel 60 is a novel element.

The protective helmet 20 may conform to protective helmets available commercially from Morning Pride Manufacturing, Inc., supra, under the LITE FORCE IV trade designation. Thus, the protective helmet 20 has a hard shell 22, which has a dome portion 24 and a rim portion 26, and the rim portion 26 projects outwardly from the dome portion 24 and has a front region 28, two side regions 30, and a back region 32. Also, the rim portion 26 is trimmed with an edge piece 34, which is made from a softer, polymeric material. Herein, references to "front", "side", and "back" are taken from a wearer's viewpoint.

The face shield 40 may conform to face shields available commercially with protective helmets available commercially from Morning Pride Manufacturing, Inc., supra. Thus, the face shield is formed from a sheet of optically clear polycarbonate so as to have a front portion 42 and two side portions 44, which portions 42, 44, are curved continuously.

The protective helmet 20 has two hinges 50, each of which is mounted to a respective one of the side regions 30 of the rim portion 26 of the hard shell 22, via two threaded fasteners 52. The face shield 40 is hinged to the protective helmet 20, via the hinges 50, so as to enable a wearer to adjust the face shield 40 between a usage position below the front region 28 of the rim portion 26 of the hard shell 22, as shown in FIG. 1, and a storage position above the front region 28 of the rim portion 26 of the hard shell 22, as shown in FIG. 2.

The hinges 50 may conform to the hinges disclosed in Lane U.S. Pat. No. 4,766,609, the disclosure of which is incorporated herein by reference. Similar hinges are employed to mount face shields to protective available commercially from Morning Pride Manufacturing, Inc., supra.

Further details of the protective helmet 20, the face shield 40, and the hinges 50 are outside the scope of this invention and can be readily supplied by persons having ordinary skill in the art.

Being a novel element, the fabric panel 60 is made from a heat-resistant, flame-resistant fabric, preferably woven from NOMEX fibers, KEVLAR fibers, or blended NOMEX and KEVLAR fibers. NOMEX and KEVLAR are trademarks for synthetic polymers available commercially from E.I. dupont de Nemours, Inc. of Wilmington, Del. Such NOMEX, KEVLAR, and blended fibers are available commercially from Southern Mills, Incorporated of Union City, Ga.

The fabric panel 60 has a portion 62 affixed to the hard shell 22 in a manner to be later described and a portion 64 extending from the affixed portion 62. The fabric panel 60 has two expansive surfaces 66, 68, which are opposite to each other. Being rectangular except for a cutout 70 to accommodate shaping of the dome portion 24 of the hard shell 22, the fabric panel 60 has two opposite edges, namely a distal edge 72 and a proximal edge 74.

The extending portion 64 of the fabric panel 60 is adapted to wrap the front portion 42 of the face shield 40 in the storage position, as in FIG. 2, and to be releasably fastened to the affixed portion 62 of the fabric panel 60 by a hook-and-loop fastener 80, in a manner to be later described, so as to form a fabric cover 90. Thus, the fabric cover 90 is adapted to protect front portion 42 of the face shield 40 against soiling, as from soot, where the front portion 42 is wrapped by the fabric panel 60.

The hook-and-loop fastener 80 comprises a hook-faced panel 82, which is sewn to the fabric panel 60, along the distal edge 72 of one expansive surface 66 of the fabric panel 60, and a loop-faced panel 84, which has a portion 86 sewn to the fabric panel 60, along the proximal edge 74 of the opposite surface 68 of the fabric panel 60, and which has a portion 88 affixed to the dome portion 24 of the hard shell 22, via an adhesive layer 88, above the front region 28 of the rim portion 26 of the hard shell 22. When the fabric panel 60 is formed into the fabric cover 90, whether or not the fabric panel 60 is wrapping the front portion 42 of the face shield 40, the hook-faced panel 82 can be detachably attached to the loop-faced panel 84.

As illustrated in FIGS. 8 through 13, a novel assembly 110 constituting another contemplated embodiment of this invention comprises a protective helmet 120, a pair of goggles 140, and a fabric panel 160. Except as explained below, the novel assembly 110 is similar to the novel assembly 10, the fabric panel 160 being a novel element.

Being similar to the protective helmet 20, the protective helmet 120 has a hard shell 122, which has a dome portion 124 and a rim portion 126, and the rim portion 126 projects outwardly from the dome portion 124 and has a front region 128, two side regions 130, and a back region 132. Also, the rim portion 126 is trimmed with an edge piece 134, which is made from a softer, polymeric material. The protective helmet 120 has two brackets 150, each being mounted to a respective one of the side regions 130 via two threaded fasteners 152 and each having a hole 154 for a purpose to be later described. The brackets 150 may conform to known brackets, which are constituent elements of the hinges 50.

Being similar to known pairs of goggles, the pair of goggles 140 comprises a lens portion 142 made from an optically clear polymer, such as polycarbonate, and a face-conforming frame 144, which is made from a more pliable polymer, such as a vinyl, and which defines two side portions 146 of the pair 140 of goggles.

Two flexible, elastic ribbons 170 are used to attach the pair 140 of goggles to side regions 130 of the rim portion 126 the protective helmet 120 so as to enable a wearer to adjust the pair 140 of goggles between a usage position beneath the front region 128 of the rim portion 126 of the hard shell 122, as shown in FIG. 8, and a storage position above the back region 132 of the rim portion 126 of the hard shell 122, as shown in FIG. 9. At a first end 172, each ribbon 170 is attached to a respective one of the side portions 146 of the pair 140 of goggles by passing the first end 162 through a labyrinthine arrangement of slots in the associated portion 146, in a known manner outside the scope of this invention. At a second end 174, each ribbon 170 passes through the hole 154 in a respective one of the brackets 150, to which such ribbon 170 is tied.

Further details of the protective helmet 120, the pair of goggles 140, the brackets 150, and the ribbons 170 are outside the scope of this invention and can be readily supplied by persons having ordinary skill in the art.

Being a novel element, the fabric panel 160 is made from a heat-resistant, flame-resistant fabric, which is similar to the heat-resistant, flame-resistant fabric employed for the fabric panel 60.

The fabric panel 160 has a portion 162 affixed to the hard shell 122 in a manner to be later described and a portion 164 extending from the affixed portion 162. The fabric panel 160 has two expansive surfaces 166, 168, which are opposite to each other. Being rectangular, the fabric panel 160 has two opposite edges, namely a distal edge 182 and a proximal edge 182. A fabric tab 186, which is made from the same fabric, is sewn to the distal edge 182 so as to extend from the distal edge 182. A reflective patch 188 of a conventional type is sewn to one expansive surface 168 of the fabric panel 160.

The extending portion 164 of the fabric panel 160 is adapted to wrap the pair of goggles 140 in the storage position, as in FIG. 9, and to be releasably fastened to the affixed portion 162 of the fabric panel 160 by a hook-and-loop fastener 200, in a manner to be later described, so as to form a fabric cover 220. The fabric cover 220 is adapted to protect the pair of goggles 140 against soiling, as from soot, where the lens portion 142 of the pair of goggles 140 is wrapped by the fabric panel 160.

The hook-and-loop fastener 200 comprises a hook-faced panel 202, which is sewn to the fabric panel 160, along the distal edge 172 of the opposite surface 166 of the fabric panel 160, and a loop-faced panel 204, which has a portion 206 sewn to the fabric panel 160, along the proximal edge 184 of the same surface 166 of the fabric panel 160, and which has a portion 208 affixed to the dome portion 124 of the hard shell 122, via an adhesive layer 210, above the front region 128 of the rim portion 126 of the hard shell 122. When the fabric panel 160 is formed into the fabric cover 220, whether or not the fabric panel 160 is wrapping the lens portion 146 of the pair of goggles 140, the hook-faced panel 182 can be detachably attached to the loop-faced panel 184.

Several alternative embodiments are shown fragmentarily in FIGS. 14, 15, and 16. In each of these embodiments, an eye protector (not shown) could be a face shield or a pair of goggles, as described above.

In the alternative embodiment of FIG. 14, a fabric panel 260 has a central portion 262 affixed adhesively to the hard shell 122 of the protective helmet 120 and two extending portions 264, 266, which extend from the central portion 262 and which can be releasably fastened so as to form a fabric cover 270 for the eye protector (not shown) via a hook-and-loop fastener 280, which has a hook-faced panel 282 sewn to an inwardly facing surface 284 of one such portion 264, near its distal edge 286, and which has a loop-faced portion 288 sewn to an outwardly facing surface 290 of the other portion 266, near its distal edge 292.

In the alternative embodiment of FIG. 15, a fabric panel 360 has a portion 362 affixed adhesively to the hard shell 122 of the protective helmet 120 and a portion 364 extending from the affixed portion 362. The extending portion 364 can be releasably fastened so as to form a fabric cover 370 for the eye protector (not shown) via a hook-and-loop fastener 380, which has a hook-faced panel 382 sewn to an outwardly facing surface 384 of the extending portion 364, near its distal edge 386, and which has a loop-faced panel 388 affixed adhesively to the hard shell 122 of the protective helmet 120. The alternative embodiment of FIG. 16 is similar to the alternative embodiment of FIG. 15 except that, in the alternative embodiment of FIG. 16, the hook-faced panel 382 of the hook-and-loop fastener 380 is sewn to an inwardly facing surface 386 of the extending portion 364.

Various other modifications may be made in either contemplated embodiment without departing from the scope and spirit of this invention.

We claim:

1. A protective helmet and eye protector assembly comprising
    (a) a protective helmet having a hard shell, the hard shell having a dome portion and a rim portion, the rim portion projecting outwardly from the dome portion and having a front region, two side regions, and a back region,
    (b) an eye protector having two side portions, each side portion being attached to the helmet so as to enable a wearer to adjust the eye protector between a usage position beneath the front region of the rim portion and a storage position, and
    (c) a fabric panel having a portion affixed to the hard shell and a portion extending from the affixed portion, the extending portion being adapted to wrap a portion of the eye protector in the storage position and to be releasably fastenable to the affixed portion so as to form a fabric cover from the fabric panel, the fabric cover being adapted to secure the eye protector in the storage position and to protect the wrapped portion of the eye protector in the storage position against soiling.

2. The protective helmet and eye protector assembly of claim 1 wherein the protective helmet has two hinges, each hinge being mounted to a respective one of the side regions of the hard shell, and wherein the eye protector is a face shield hinged to the protective helmet, via the hinges, so as to enable a wearer to adjust the face shield between the usage position and the storage position.

3. The protective helmet and eye protector assembly of claim 2 wherein the storage position is above the front region of the hard shell.

4. The protective helmet and eye protector assembly of claim 1 wherein the eye protector is a pair of goggles having a pair of ribbons, each ribbon extending between a respective one of the side portions of the pair of goggles and the helmet, so as to enable a wearer to adjust the pair of goggles between the usage position and the storage position.

5. The protective helmet and eye protector assembly of claim 3 or 4 comprising (d) at least one fastener adapted to fasten the extending portion of the fabric panel releasably to the affixed portion of the fabric panel so as to form the fabric cover from the fabric panel.

6. The protective helmet and eye protector assembly of claim 5 wherein said fastener is a hook-and-loop fastener.

7. The protective helmet and eye protector of claim 6 wherein the hook-and-loop fastener includes a hook-faced panel and a pile-faced panel, one said fastener panel being sewn to the extending portion of the fabric panel, the other fastener panel having a portion sewn to the fabric panel and a portion affixed adhesively to the dome portion of the hard shell.

8. The protective helmet and eye protector of claim 7 wherein the fabric panel has two expansive surfaces and wherein the hook-faced and loop-faced panels are sewn to the same one of the expansive surfaces.

9. The protective helmet and eye protector assembly of claim 4 wherein the storage position is above the back region of the hard shell.

10. The protective helmet and eye protector assembly of claim 1 or 2 comprising (d) at least one fastener adapted to fasten the extending portion of the fabric panel releasably to the affixed portion of the fabric panel so as to form the fabric cover from the fabric panel.

11. The protective helmet and eye protector assembly of claim 10 wherein said fastener is a hook-and-loop fastener.

12. The protective helmet and eye protector of claim 11 wherein the hook-and-loop fastener includes a hook-faced panel and a pile-faced panel, one said fastener panel being sewn to the extending portion of the fabric panel, the other fastener panel having a portion sewn to the fabric panel and a portion affixed adhesively to the dome portion of the hard shell.

13. The protective helmet and eye protector of claim 12 wherein the fabric panel has two expansive surfaces and wherein the hook-faced and loop-faced panels are sewn to opposite ones of the expansive surfaces.

14. A protective helmet and eye protector assembly comprising (a) a protective helmet having a hard shell, the hard shell having a dome portion and a rim portion, the rim portion projecting outwardly from the dome portion and having a front region, two side regions, and a back region, (b) an eye protector having two side portions, each side portion being attached to a respective one of the side regions of the rim portion of the helmet so as to enable a wearer to adjust the eye protector between a usage position beneath the front region of the rim portion and a storage position above the rim portion, and (c) a fabric panel having a portion affixed to the hard shell and a portion extending from the affixed portion, the extending portion being adapted to wrap the eye protector in the storage position and to be releasably fastenable so as to form a fabric pouch from the fabric panel, the fabric pouch being adapted to secure the eye protector in the storage position and to protect the eye protector in the storage position against soiling where wrapped by the fabric panel.

* * * * *